US005650560A

United States Patent [19]

Troost

[11] Patent Number: 5,650,560
[45] Date of Patent: Jul. 22, 1997

[54] METHOD AND APPARATUS FOR ANALYZING GASES CONTAINING VOLATILE ORGANIC COMPOUNDS BY USE OF TETRAGLYME

[75] Inventor: John R. Troost, Meraux, La.

[73] Assignee: Southern Petroleum Laboratories, Inc., Houston, Tex.

[21] Appl. No.: 443,366

[22] Filed: May 17, 1995

[51] Int. Cl.$^6$ ............................ B01D 53/14; G01N 1/00
[52] U.S. Cl. ............ 73/23.41; 73/31.07; 73/31.02; 73/31.03; 55/256; 95/226; 261/121.1; 436/178
[58] Field of Search .................... 73/23.41, 23.38, 73/31.01, 31.02, 31.03, 31.07; 55/356; 95/226; 261/121.1; 422/88, 89; 436/178

[56] References Cited

U.S. PATENT DOCUMENTS

| | | | |
|---|---|---|---|
| 2,257,170 | 9/1941 | Howell | 436/178 |
| 3,642,431 | 2/1972 | Suzuki et al. | 423/226 |
| 3,656,887 | 4/1972 | Suzuki et al. | 423/226 |
| 3,778,968 | 12/1973 | Parker, Sr. | 95/226 |
| 4,976,935 | 12/1990 | Lynn | 423/222 |
| 4,995,888 | 2/1991 | Beaupre et al. | 95/46 |

FOREIGN PATENT DOCUMENTS

| 682253 | 8/1979 | U.S.S.R. | 55/256 |
|---|---|---|---|

*Primary Examiner*—Hezron E. Williams
*Assistant Examiner*—Daniel S. Larkin
*Attorney, Agent, or Firm*—N. Elton Dry

[57] ABSTRACT

A method and apparatus for sampling and analyzing gas. In particular landfill gas, which consists primarily of methane and contains volatile organic components, is passed through a quantity of liquid tetraglyme to cause the volatile organic components to be absorbed in the tetraglyme. The tetraglyme containing the absorbed volatile organic components, is then disposed in a sealed container and transported to a laboratory testing facility. At the testing facility, at least a portion of the tetraglyme is withdrawn from the container, dispersed in water, and subjected to a gas chromatography/mass spectrometry procedure to analyze the volatile organic components.

14 Claims, 3 Drawing Sheets

METHOD AND APPARATUS FOR ANALYZING GASES CONTAINING VOLATILE ORGANIC COMPOUNDS BY USE OF TETRAGLYME

TECHNICAL FIELD OF THE INVENTION

This invention relates in general to a method and system of sampling and analyzing a gas for organic and inorganic pollutants. More specifically, the invention relates to a method of sampling and analyzing ambient air or landfill gas, particularly methane, for volatile organic compounds.

BACKGROUND OF THE INVENTION

The Clean Air Act requires the sampling of gases, including ambient air and landfill gas, and the analysis of those samples for a variety of volatile organic and inorganic compounds. One problem with the sampling and analysis requirements of the Clean Air Act has been that the required detection limits of volatile organics in gas have often exceeded the capability of existing technology.

For example, gas generated through the decomposition of waste in landfills consists primarily of methane, along with volatile organic compounds. The volatile organic compounds can consist of hydrocarbons, which are relatively inert, or can be halogen compounds containing chlorine, bromine, fluorine, or iodine, which are reactive. In addition, the volatile organic compounds may include aromatic hydrocarbons, such as benzene, toluene, xylene, and the like, which are classified as carcinogenic. The type and concentration of the volatile organic compounds can vary from site-to-site, depending upon the nature of the waste in the landfill.

It has been the practice, in the past, to vent the gas from the landfill. In a typical installation, a number of perforated wells or pipes are distributed throughout the landfill to collect the gas, and the gas is then conducted to a manifold or header for discharge from the landfill. As the landfill gas consists primarily of methane, it has been proposed to use the landfill gas as a fuel for gas aspirated internal combustion engines. The engines can be used at the landfill site for generating electricity or steam, pumping, or other functions. At a typical landfill there may be from two to six engines that are operating on the landfill gas.

The presence of certain volatile organic compounds in the landfill gas, particularly the halogenated compounds, can cause serious problems with operation of the engine. Due to the reactivity of these compounds, they can react with other constituents to form acids which can attack or corrode engine bearings, bushings, valve guides and stems, as well as producing deposits on the valve seats, and deterioration of the engine oil.

Because of these potential problems with the use of landfill gas, it is important to determine the type and concentration of the volatile organic compounds in the landfill gas. If it is found that the landfill gas has a high concentration of volatile organic compounds that could have a deleterious effect on engine operation, steps can be taken to reduce the concentration of the volatile organic compounds by flaring-off the gas for an extended period, or alternatively, treating the gas by catalytic processes to remove or reduce the volatile organic compounds to acceptable limits.

In order to sample and analyze the landfill gas prior to using the gas as a fuel for an internal combustion engine, several methods have been employed under the Clean Air Act.

It has been proposed to collect the landfill gas or ambient air in plastic or metal containers, and ship the containers to a laboratory for analysis, using a standard gas chromatography/mass spectrometry (GC/MS) procedure. However, it has been found that the volatile organic compounds tend to "plate out" on the plastic or metal containers, with the result that the analysis is flawed and results in a lesser and inaccurate determination of the concentration of the volatile organic compounds.

It has also been proposed in the past to sample and analyze the landfill gas or ambient air by a Tenax® tube method. In this method, a quantity of granular aluminum oxide is contained within a small tube, approximately four inches long, and the landfill gas is fed through the tube, and the volatile organic compounds will be adsorbed on the granular material. The tube is then sealed and shipped or transported to a laboratory for analysis. To analyze the material, the tube is uncapped and the granular material is heated through induction heating to vaporize the adsorbed contaminants, which are then subjected to the standard GC/MS analysis.

The Tenax® tube sampling method has several disadvantages. First, the sampling method has a relatively short shelf life, in that the volatile organic compounds tend to migrate or desorb from the granular aluminum oxide carrier, so that when the shipping container is opened, the volatilized compounds will escape, so that the resulting analysis is flawed.

Secondly, the Tenax® tube sampling system is a "one shot" procedure, in which all of the gas released from the granular material on the induction heating is used for a single analysis in the GC/MS procedure. There is no capability of using only a portion of the volatilized gas in order to run additional tests to verify the results.

Further, the Tenax® tube sampling system also requires that the laboratory have thermal desorption equipment in order to vaporize and release the volatile organic compounds from the Tenax® material. It has been found that not all analysis laboratories have such equipment.

Therefore, there has been a distinct need for a simple and effective method of accurately sampling and analyzing landfill gas that could be repeated by different laboratories using standard sampling and analytical techniques.

SUMMARY OF THE INVENTION

The invention is directed to a method of sampling and analyzing a gas containing volatile organic compounds and particularly to a method of sampling and analyzing landfill gas. In accordance with the invention, a given volume of gas is passed serially through one or more impingers, each containing a quantity of liquid tetraglyme. The gas is bubbled up through the tetraglyme and the volatile organic compounds are absorbed in the tetraglyme.

To increase the efficiency of the absorption, it is preferred to chill the tetraglyme to a temperature below 0° C. and preferably in the range of about 0° C. to −30° C. The low temperature will minimize volatilization of certain volatile organic compounds that have low boiling points. After the given volume of gas has passed through the tetraglyme, the tetraglyme is transferred to a sealed container.

The gas sampling device of the present invention comprises at least one impinger containing tetraglyme and a means for percolating the gas through the tetraglyme. The gas sampling device may also contain the means for controlling the temperature of the tetraglyme, as for example an insulated container filled with salted ice surrounding the impingers. One embodiment of the sampling device is a portable field sampling unit.

At the site of analysis, at least a portion of the tetraglyme is withdrawn from the sealed container, mixed with water, and subjected to a standard gas chromatography/mass spectrometry (GC/MS) instrumentation to obtain an analysis of the volatile organic compounds. With the invention, detection limits of 1 mg/m$^3$ for organic compounds can be achieved when sampling a volume of landfill gas in the order of six liters.

The tetraglyme has a powerful affinity for organic compounds and will act to trap and retain the targeted volatile organic compounds with simplicity and low cost. With the method of the invention, the analysis can be made by any laboratory having the GC/MS instrumentation.

Since refrigerated tetraglyme has been shown to retain the trapped volatile compounds for extended periods of time, the analysis may be carried out long after the sampling without adversely effecting the integrity of the analysis.

In addition, only a portion of the tetraglyme need be analyzed at any one time and this enables additional portions to be subsequently analyzed to verify the original results.

Furthermore, tetraglyme absorption of volatile organics can replace the following clean air methods for ambient air sampling and analysis: (a) T01 "Determination of Volatile Organic Compounds in Ambient Air Using Tenax® Adsorbtion and Gas Chromatography/Mass Spectrometry (GC/MS)", (b) T02 "Determination of Volatile Organic Compound in Ambient Air by Carbon Molecular Sieve Adsorption and Gas Chromatography/Mass Spectrometry (GC/MS)", (c) T03 "Determination of Volatile Compounds in Ambient Air Using Cryogenic Preconcentration Techniques and Gas Chromatography with Flame Ionization and Electron Capture Detection" and (d) T014 "Determination of Volatile Organic Compounds (VOCS) in Ambient Air Using Summa® Passivated Canister Sampling and Gas Chomatographics Analysis."

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The present invention can increase the sensitivity and accuracy of ambient air and gas analysis for volatile organic and inorganic compounds.

For example, landfill gas has become an increasingly popular fuel; yet the complicated nature of the composition of the landfill gas has not permitted the industry to define precise standards for sampling, analyzing or using the gas as a fuel. Landfill gas consists primarily of methane, along with various volatile organic compounds and, in some cases, volatilized inorganic compounds. A typical landfill gas may contain halogenated volatile organic compounds, such as chlorobenzene, dichlorobenzene, dichlorethane, dichloroethene, chloromethane, methylene chloride, tetrachloroethane, trichloroethane, trichloroethane, vinyl chloride, and the like. In addition, the landfill gas may also include aromatic hydrocarbons, such as benzene, styrene, toluene, xylene, and the like. Siloxane compounds, such as octamethyl cyclotetrasiloxane and decamethyl cyclopentasiloxane may also be present.

The halogenated volatile organic compounds are particularly troublesome when using the landfill gas as a fuel for an internal combustion engine. These compounds are reactive and can react with other constituents in the gas to form acids, which can corrode the bearings, bushings, and valve guides and stems of the engine. In addition, the halogenated organic compounds can also produce deposits on the valve seats, and can deteriorate the engine oil. Because of this, it is desirable to sample and analyze the landfill gas prior to using the gas as a fuel for the engine, as well as sampling and analyzing the gas periodically during operation of the engine.

In a typical landfill operation, a number of perforated wells, or pipes, are located in a random pattern throughout the landfill and are used to collect the landfill gas. The wells are connected to a common manifold or header, and that gas is then distributed from the header to one or more engines that are located at the landfill site. In a typical installation, the suction side of a pump is connected to the manifold, and the gas is pumped, under pressure, by the pump to the engine. Before being introduced to the engine, it is also customary to remove moisture from the landfill gas, such as by passing the gas through a chiller.

In accordance with the invention, a novel sampling and analyzing method is provided in order to determine the type and concentration of various volatile compounds in the gas which could have a deleterious effect on engine operation.

Figure 1:
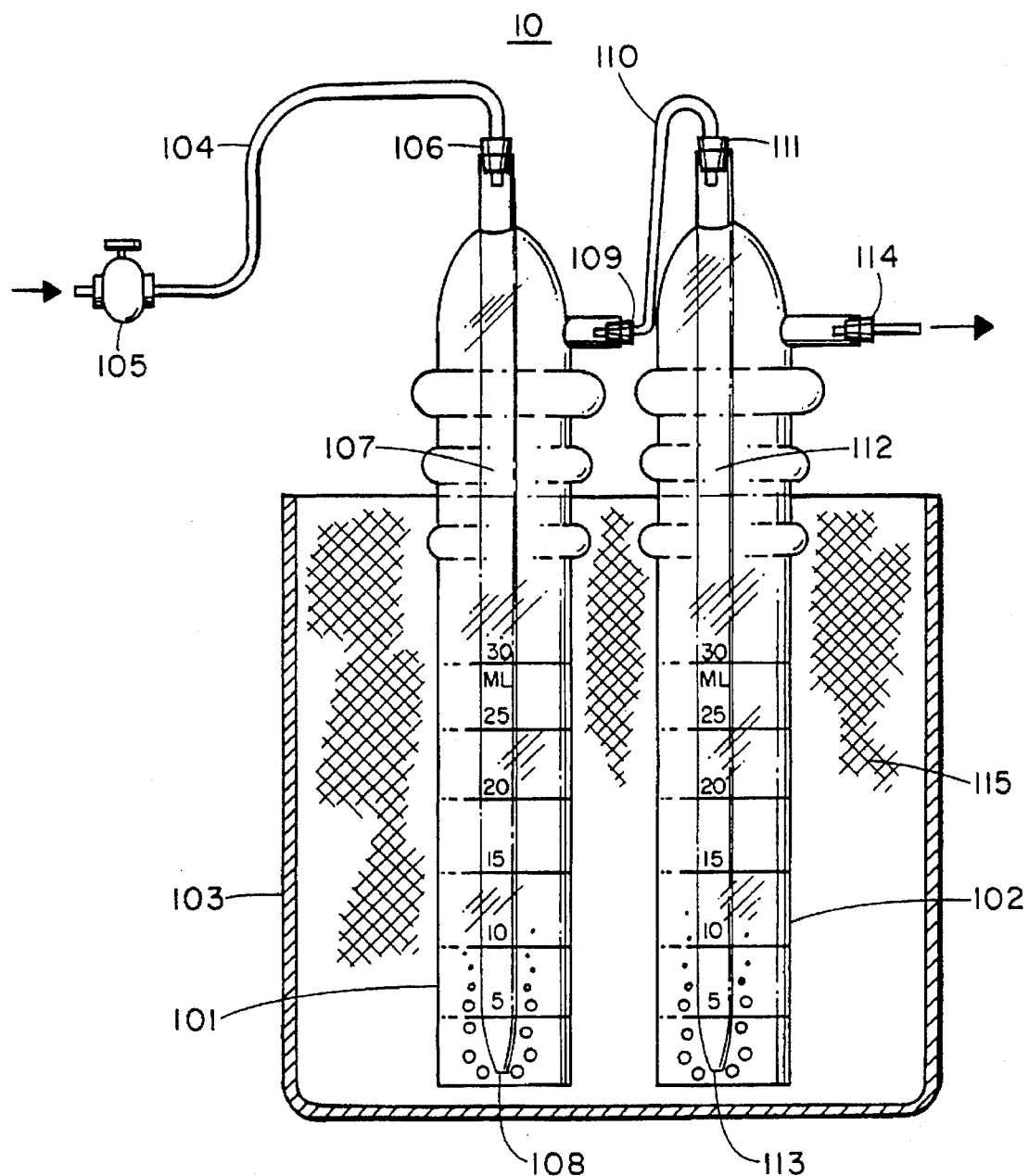
FIG. 1 is a diagrammatic view of one embodiment of a gas sampling device.

FIG. 1 shows a preferred embodiment of a gas sampling device 10 which can be used to sample a quantity of gas such as ambient air, smoke stack discharge, landfill gas, etc. The sampling device 10 may be made of one or more impingers filled with a desired volume of tetraglyme (tetraethylene glycol dimethyl ester). Tetraglyme is an organic solvent, soluble in water, with a boiling point of 276° C.

Tetraglyme has a high affinity for polar and non-polar, low and high boiling, halogenated and non-halogenated, aromatic and aliphatic organic compounds.

Referring now to FIG. 1, the illustrated sampling device 10 includes two impingers, impingers 101 and 102, each filled with about 25 to 30 ml. of tetraglyme. Impingers 101 and 102 are mounted in an open-top container or tank 103. An inlet line 104 is typically connected to a pressurized source of the gas to be analyzed, and a valve 105, preferably a needle valve, is mounted in line 104, and serves to control the flow of the gas through line 104 to impinger 101.

As shown in the drawing, line 104 is connected to a fitting 106, which is mounted in the upper end of impinger 101, and a tube 107 is mounted concentrically within the impinger and is provided with an outlet 108 in its lower end. The gas entering the impinger 101 through fitting 106 will flow downwardly through tube 107, and is discharged through outlet 108, bubbling upwardly through the quantity of tetraglyme contained in impinger 101. Optionally, any water vapor in the gas entering the impinger 101 may be removed prior to passing the gas through the tetraglyme.

As the gas flows upwardly through the tetraglyme in impinger 101, the volatile, organic compounds will be absorbed in the tetraglyme. The gas is then discharged from the upper end of impinger 101 through an outlet fitting 109, and is conducted through a hose or line 110 to the inlet fitting 111 of impinger 102. Impinger 102 is constructed in the same manner as impinger 101, and includes a central tube 112, having an outlet 113 in its lower end. The gas flows downwardly through tube 112, and is discharged through outlet 113, flowing upwardly through the tetraglyme contained within the impinger 102, to thereby cause absorption of the volatile compounds in the tetraglyme. The gas is then discharged through outlet fitting 114 in the upper end of impinger 102 to the atmosphere, or other site.

The gas flowing through impinger 101 and 102 is pressurized, and normally is at a pressure in the range of about 2 to 8 psi, and preferably about 5 psi. In practice, about six liters of gas are passed through impingers 101 and 102, and through operation of the valve 105, the flow rate of the gas is generally in the range of about 50 to 500 ml per minute, and preferably about 100 ml per minute.

It has been found that the retention and detection limits for several of the volatile organic compounds can be improved by maintaining the tetraglyme at a low temperature, preferably below 0° C., and generally in the range of about 0° C. to −30° C. This low temperature can be achieved by locating impingers 101 and 102 within an ice bath 115 or a salt/ice bath in container 103.

The use of the low temperature will minimize volatilization of certain volatile organic compounds that have low boiling pints, such as chloromethane, vinyl chloride and chloromethane. In addition, lowering the temperature of the tetraglyme will increase its viscosity, so that the gas will bubble through the tetraglyme at a slower rate, thus increasing the residence time of the gas within the tetraglyme.

While the drawing shows two impingers being employed, it is contemplated that one or more impingers may be used. The advantage of multiple impingers is that volatile compounds, which may not have been absorbed by the tetraglyme in the first impinger in the series, may be absorbed in the tetraglyme in the second impinger, thus increasing the efficiency of the sampling.

After the desired volume of gas has been passed through the impingers 101 and 102, the tetraglyme is poured from the impingers into a shipping container or tube, and sealed within the tube. The low boiling point organic compounds will not volatilize and will be retained in the tetraglyme.

Tetraglyme serves as a superior solvent for solubilizing, shipping and storing volatile organic reference standards, or analytical standards. Solutions of volatile organic standards made up in tetraglyme have a longer shelf life than standards made up in other known solvents and stored in a shipping container at ambient temperatures. Examples of volatile organic compounds that have improved sample integrity when dissolved and stored in tetraglyme are acetone, benzene, chlorobenzene, chloroethane, dichlorobenzene, dichloroethane, dichloroethene, ethylbenzene, 2-hexanone, chloromethane, methylene chloride, 2-butanone, methylpentanone, styrene, tetrachloroethene, toluene, trichloroethane, trichloroethene, vinyl chloride, xylene, octamethyl cyclotetrasiloxane, decamethyl cyclopentasiloxane, and mixtures thereof. Volatile organic compounds dissolved in other solvents will often "plate out" or adsorb to the surface of the shipping container, yielding an artificially decreased concentration of the volatile organic compounds being measured.

The tetraglyme in the shipping container is then transported on ice to a suitable laboratory site for analysis using a standard gas chromatography/mass spectrometry (GC/MS) procedure, as set forth in EPA method 8240. In performing the analysis, a portion of the tetraglyme containing the absorbed volatile organic compounds is removed from the shipping container and dispersed in water, preferably in a ratio of about 100 microliters of tetraglyme per 5 ml of water. This sample is then subjected to standard GC/MS instrumentation to obtain an analysis of the volatile organic compounds.

With the invention, detection limits of 1 mg/m$^3$ of organic compounds can be achieved when sampling six liters of the landfill gas. Even lower detection limits can be achieved by using greater volumes of gas, or by dispersing greater quantities of tetraglyme into water, as for example, using 500 ml of tetraglyme with 25 ml of water for the analysis.

The method of the invention can also detect inorganic contaminants in the gas, but the inorganics must be present in a vaporized form, or be attached to air borne particulates.

The invention provides distinct advantages over prior sampling and analyzing methods for landfill gas. The tetraglyme impingers effectively trap and retain all of the targeted volatile organic compounds with simplicity and low cost. The chilled tetraglyme has a powerful affinity for all pollutants and hazardous substance list volatile organics, including polar, non-polar, high and low boiling, halogenated and non-halogenated, and aromatic and aliphatic materials.

The sampling method of the invention using the tetraglyme provides samples with a substantially greater shelf life than prior sampling methods, so that the time period between the sampling and analysis is not as critical.

As a further advantage, only a portion of the tetraglyme need be analyzed at any one time, and this enables additional portions of the tetraglyme to be subsequently analyzed to verify the original results. This differs from prior methods, in which it was necessary to analyze the entire sample, so that there was no remaining portion of the sample that could be subsequently analyzed for verification.

Further, with the method of the invention, the characterization of the volatile organics can be made by routine water analysis GC/MS methodologies, so that the analysis can be performed by any laboratory having ordinary GC/MS instrumentation.

The invention also preserves the sample integrity, in that there is no possibility of the volatile organic compounds plating out on the wall of any container during shipment or handling.

Figure 2:
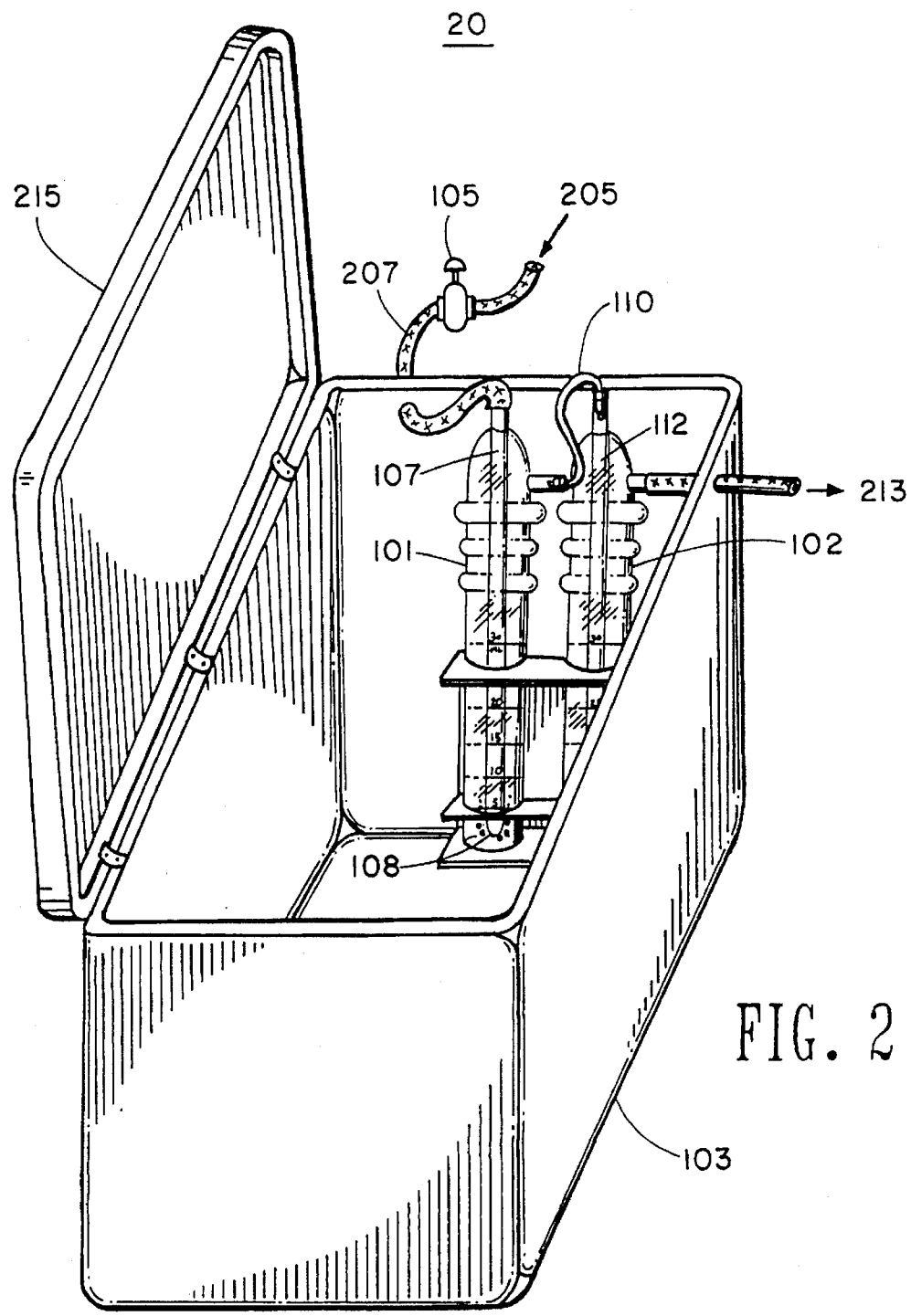
FIG. 2 is a diagrammatic view of one embodiment of a field sampling unit.
Figure 3:
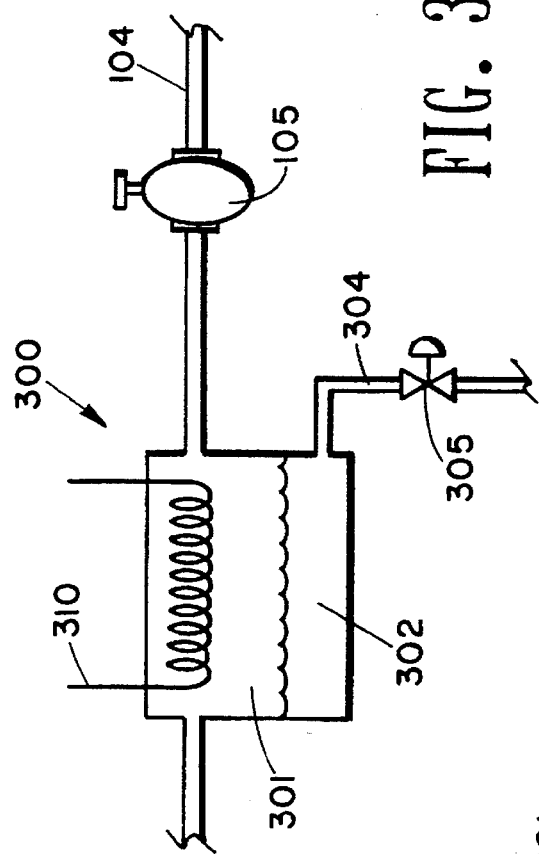
FIG. 3 is a schematic showing chiller unit 300, having chiller 310, tank 301 for gathering condensate 302, and drain line 304 and valve 305, located upstream from valve 105.
Figure 4:
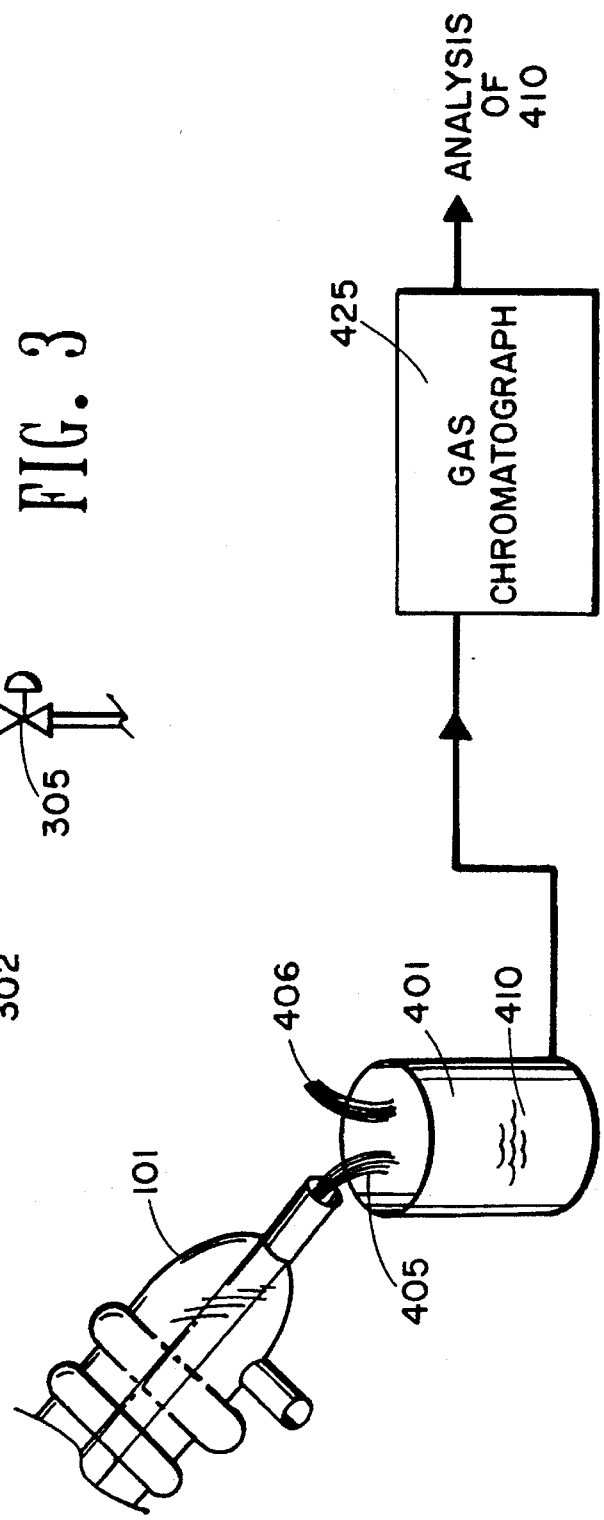
FIG. 4, is a schematic showing the pouring of tetraglyme 405 from impinger 101 and addition of water 406, both into shipping container or tube 401, to form a dispersion 410, which dispersion 410 is then analyzed in gas chromatograph 425.

FIG. 2 shows a preferred embodiment of a field sampling device 20. The field sampling device 20 contains one or more impingers containing a predetermined quantity of tetraglyme. The construction of the impingers is the same as the gas sampling device 10 shown in FIG. 1.

The field sampling device 20 shown in FIG. 2 has two impingers, impingers 101 and 102, mounted in an insulated container 103. An inlet 205 is connected to a gas source and the flow rate of that gas into impinger 101 is controlled by valve 105 mounted in line 207. The flow rate can be estimated using a portable bubble meter and adjusted with valve 105. Line 207 carries gas to the upper end of impinger 101 and into a tube 107 mounted concentrically within impinger 101. Tube 107 has an outlet 108 at the lower end of impinger 101. As the gas flows downward through tube 107 and is discharged through outlet 108, it bubbles through the tetraglyme in impinger 101 to rise to the surface and is conducted through a hose 110 and into impinger 102. Impinger 102 is constructed in the same manner as impinger 101, and includes a central tube 112.

As the gas enters impinger 102, it is carried down central tube 112 and is discharged through an opening at the bottom end of tube 112 (not shown). The gas bubbles up through the tetraglyme and can be released into the atmosphere, or elsewhere through outlet 213.

The field sampling device 20 includes an insulated container 103 which can hold a mixture of ice or ice and salt to keep the tetraglyme cold. The field sampling device 20 can be built relatively inexpensively and can be used multiple times as long as impingers 101 and 102 are washed thoroughly with soap and water between uses.

Optionally, the field sampling device 20 may include a portable bubble meter and shipping containers for the samples. The entire field sampling device 20 may be conveniently packaged in container 103 having a hinged lid 215 to provide an enclosed, secure package that is easily transported. The field sampling device 20 provides an inexpensive, portable apparatus that can be used to provide sensitive and accurate gas sampling at any site location.

Although the present invention and its advantages have been described in detail, it should be understood that various changes, substitutions and alterations can be made herein without departing from the spirit and scope of the invention as defined by the appended claims.

What is claimed is:

1. A method of sampling and analyzing a gas containing volatile organic compounds, comprising the steps of passing the gas through a quantity of liquid tetraglyme to cause the volatile organic compounds to be absorbed in the tetraglyme, removing at least a portion of the tetraglyme from the container and mixing said tetraglyme with water to form a dispersion, and thereafter subjecting the dispersion to gas analysis to identify the volatile organic compounds.

2. The method of claim 1, and including the step of maintaining the tetraglyme at a temperature below 0° C. when the gas is passed through said tetraglyme.

3. The method of claim 1, and including the step of passing a preselected volume of gas through said tetraglyme.

4. The method of claim 1, and including the step of disposing the tetraglyme in an impinger, said step of passing the gas through the tetraglyme comprises percolating the gas through the tetraglyme in said impinger.

5. The method of claim 1, and including the step of disposing the tetraglyme in a plurality of individual impingers, said step of passing the gas through the tetraglyme comprising percolating the gas through each impinger.

6. A method of sampling and analyzing landfill gas, comprising conducting gas comprising methane and containing volatile organic compounds from a landfill site, passing a preselected volume of said gas through a quantity of liquid tetraglyme in a container to thereby absorb said volatile organic compounds in said tetraglyme, withdrawing at least a portion of the tetraglyme from the container and mixing the tetraglyme with water to form a mixture, and subjecting the mixture to a gas chromatography/mass spectrometry analysis to analyze the composition of said volatile organic compounds.

7. The method of claim 6, and including the step of maintaining the temperature of said tetraglyme at a value in the range of 0° C. to −30° C.

8. The method of claim 6, and including the step of removing water vapor from said gas prior to passing the gas through said tetraglyme.

9. The method of claim 6, wherein said gas is passed through said quantity of tetraglyme at a flow rate of about 50 to 500 ml/minute.

10. A method of sampling and analyzing landfill gas, comprising conducting landfill gas composed of methane and volatile organic compounds from a landfill site, removing water vapor from said gas, passing a preselected volume of said gas through a quantity of liquid tetraglyme contained within an impinger and flowing the gas upwardly through said quantity of tetraglyme to thereby cause the volatile organic compounds to be absorbed in said tetraglyme, transferring the tetraglyme with the absorbed volatile organic compounds to a container, icing down the container, transferring the container to an analysis site, withdrawing at least a portion of the tetraglyme from the container at the analysis site, and subjecting the withdrawn tetraglyme to a gas chromatography/mass spectrometry procedure to analyze the composition of said volatile organic compounds.

11. An apparatus for extracting volatile organic impurities from a gas sample; said apparatus comprising:

a plurality of impingers, said impingers containing an amount of tetraglyme;

means for introducing said gas sample into each impinger;

means for placing said gas in contact with the tetraglyme;

means for controlling the temperature of said tetraglyme; and means for recovering the gas sample from the impingers, subsequent to contact with the tetraglyme.

12. The apparatus of claim 11, wherein said temperature controlling means is an insulated container containing a substance at a temperature of less than 0° C.

13. The apparatus of claim 11, wherein said apparatus is portable.

14. The apparatus of claim 11, further comprising a means for controlling the flow rate of said gas into said impingers.

* * * * *